United States Patent
White et al.

(10) Patent No.: US 7,157,696 B2
(45) Date of Patent: *Jan. 2, 2007

(54) TEST OBJECT FOR CALIBRATION OF IMAGING MEASUREMENTS OF MAMMALIAN SKELETAL JOINTS

(75) Inventors: David L. White, Oakland, CA (US); Manish Khotari, San Francisco, CA (US); Richard A. Carano, San Ramon, CA (US)

(73) Assignee: Synarc, Inc., San Francisco, CA (US)

( * ) Notice: Subject to any disclaimer, the term of this patent is extended or adjusted under 35 U.S.C. 154(b) by 131 days.

This patent is subject to a terminal disclaimer.

(21) Appl. No.: 10/870,686

(22) Filed: Jun. 17, 2004

(65) Prior Publication Data

US 2005/0139758 A1     Jun. 30, 2005

Related U.S. Application Data

(63) Continuation-in-part of application No. 10/388,118, filed on Mar. 12, 2003, now Pat. No. 6,992,280.

(60) Provisional application No. 60/370,019, filed on Apr. 4, 2002.

(51) Int. Cl.
*G01D 18/00* (2006.01)

(52) U.S. Cl. ............... 250/252.1; 378/207; 324/300; 73/1.86

(58) Field of Classification Search ............ 250/252.1; 378/207; 324/300; 73/1.86
See application file for complete search history.

(56) References Cited

U.S. PATENT DOCUMENTS

| 4,719,406 | A | * | 1/1988 | Schaefer et al. ............ 324/318 |
| 4,818,943 | A | * | 4/1989 | Chandra ..................... 324/318 |
| 5,299,253 | A | | 3/1994 | Wessels |
| 5,416,816 | A | | 5/1995 | Wenstrup et al. |
| 6,205,871 | B1 | | 3/2001 | Saloner et al. |
| 6,409,515 | B1 | | 6/2002 | Persohn et al. |
| 6,629,469 | B1 | | 10/2003 | Jaszczak et al. |
| 6,675,035 | B1 | | 1/2004 | Grable et al. |
| 6,992,280 | B1 | * | 1/2006 | White et al. ............. 250/252.1 |

OTHER PUBLICATIONS

Barker et al., "Semiautomated quality assurance for quantitative magnetic resonance imaging," *Magn. Reson. Imaging*, 10(4):585-595 (1992).

Berns et al., "The accuracy of signal intensity measurements in magnetic resonance imaging as evaluated within the knee," *Magn. Reson. Imaging*, 10(4):573-578 (1992).

Bland et al., "Robust three-dimensional object definition in CT and MRI," *Med. Phys.*, 23(1):99-107 (1996).

Bondestam et al., "Magnetic resonance imaging of transfusional hepatic iron overload," *Br. J. Radiol.*, 67(796):339-341 (1994).

Coffey et al., "A slice geometry phantom for cross sectional tomographic imagers," *Med. Phys.*, 16(2):273-278 (1989).

(Continued)

*Primary Examiner*—Albert Gagliardi
(74) *Attorney, Agent, or Firm*—Townsend and Townsend and Crew LLP

(57) ABSTRACT

The invention provides a test device or "phantom" for use in conjunction with medical imaging modalities. In one embodiment, the phantom replicates the attenuation and absorption properties of joint articular cartilage. The phantom is useful for quality assurance of images of joints obtained using an array of medical imaging modalities.

34 Claims, 5 Drawing Sheets

OTHER PUBLICATIONS

Decarli et al., "Local histogram correction of MRI spatially dependant image pixel intensity nonuniformity," *J. Magn. Reson, Imaging*, 6(3):519-528 (1996).

Disler et al., "Accuracy of Volume Measurements of Computed Tomography and Magnetic Resonance Imaging Phantoms by Three-Dimensional Reconstruction and Preliminary Clinical Application," *Invest. Radiology*, 29(8):739-745 (1994).

Drangova et al., "Physiologic motion phantom for MRI applications," *J. Magn. Reson. Imaging*, 6(3):513-518 (1996).

Engelke et al., "Phantom Studies simulating the impact of trabecular structure on marrow relaxation time T2'," *Magn. Reson. Med.*, 31(4):380-387 (1994).

Fellner et al., "A high-resolution phantom for MRI," *Magn. Reson. Imaging*, 19(6):899-904 (2001).

Firbank et al., "Quality assurance for MRI: practical experience," *Br. J. Radiol.*, 73(868):376-383 (2000).

Firbank et al., "Partial Volume Effects In MRI Studies Of Multiple Sclerosis," *Magn. Reson. Imaging*, 17(4):593-601 (1999).

Hendrich et al., "Surface coil cardiac tagging and 31P spectroscopic localization with B1-insensitive adiabatic pulses," *Magn. Reson. Med.*, 31(5):541-545 (1994).

Hittmair et al., "Method for the quantitative assessment of contrast agent uptake in dynamic contrast-enhanced MRI," *Magn. Reson. Med.*, 31(5):567-571 (1994).

Kalender et al., "A comparison of conventional and spiral CT: an experimental study on the detection of spherical lesions," *J. Comput. Assist Tomogr.*, 18(2):167-176 (1994).

Kjaer et al., "Evaluation of relaxation time measurements by magnetic resonacnce imaging. A phantom study.," *Acta Radiol.*, 28(3):345-351 (1987).

Kraft et al., "An MRI phantom material for quantitative relaxometry," *Magn. Reson. Med.*, 5(6):555-562 (1987).

Laubach et al., "A Phantom for Diffusion-Weighted Imaging of Acute Stroke," *J. Magn. Reson. Imaging*, 8:1349-1354 (1998).

Luft et al., "Reliability and exactness of MRI-based volumetry: a phantom study," *J. magn. Reson. Imaging*, 6(4):700-704 (1996).

Madsen et al., "Low-contrast focal lesion detectability phantom for 1H MR imaging," *Med. Phys.*, 18(3):549-554 (1991).

Maeda et al., "Partial volume effect in MRI—a phantom study," *Nippon Igaku Hoshasen Gakkai Zasshi*, 49(11):1404-1410 abstract only (1989).

Orth et al., "Development of a unique phantom to assess the geometric accuracy of magnetic resonance imaging for stereotactic localization," *Neurosurgery*, 45(6):1423-1429 (1999).

Pabst et al., "Understanding why contrast enhancement in dynamic MRI is not reproducible: illustration with a simple phantom," *Breast J.*, 7(3):166-170 (2001).

Peterfy, C. G., "Role of MR imaging in clinical research studies," *Semin. Musculoskelet. Radiol.*, 5(4):365-378 abstract only (2001).

Prott et al., "Comparison of imaging accuracy at different MRI units based on phantom measurements," *Radiother. Oncol.*, 37(3):221-224 (1995).

Reeder et al., "Tag contrast in breath-hold CINE cardiac MRI," *Magn. Reson. Med.*, 31(5):521-525 (1994).

Rubin et al., "Optimization of an oral magnetic particle foprmulation as a gastrointestinal contrast agent for magnetic resonance imaging," *Invest. Radiol.*, 29(1):81-86 (1994).

Stoller, D. W., "Knee," Chapter 61, pp. 1954-2003 from *Clinical Magnetic Resonance Imaging*, Edleman et al., eds., (1996).

Taylor et al., "A simple phantom to locate the origin of MRI ghost artefacts," *Magn. Reson. Imaging*, 16(1):73-76 (1998).

Tofts et al., "An oblique cylinder contrast-adjusted (OCCA) phantom to measure the accuracy of MRI brain lesion volume estimation schemes in multiple sclerosis," *Magn. Reson. Imaging*, 15(2):183-192 (1997).

Velthuizen et al., "Review and evaluation of MRI nonuniformity corrections for brain tumor response measurements," *Med. Phys.*, 25(9):1655-1666 (1998).

White et al., "A Phantom for Quality Control of MRI Knee Cartilage Volume Measurements in Clinical Trials," *Proc. Intl. Soc. Mag. Reson. Med. 9*, (2001).

Yu et al., "A phantom study of the geometric accuracy of computed tomographic and magnetic resonance imaging stereotactic localization with the Leksell stereotactic system," *Neurosurgery*, 48(5):1092-1098 (2001).

* cited by examiner

End View

Top View

End View

Top View

TEST OBJECT FOR CALIBRATION OF IMAGING MEASUREMENTS OF MAMMALIAN SKELETAL JOINTS

CROSS-REFERENCES TO RELATED APPLICATIONS

This application is a continuation-in-part of U.S. patent application Ser. No. 10/388,118, filed Mar. 12, 2003, now U.S. Pat. No. 6,992,280, which claimed priority to U.S. Provisional Patent Application Ser. No. 60/370,019, filed Apr. 4, 2002, the complete disclosures of which are incorporated herein by reference.

BACKGROUND OF THE INVENTION

The present relates generally to imaging test objects or "phantoms." More specifically, the present invention is related to phantoms that are used to simulate joints and joint cartilage.

A phantom is a device that simulates a body of tissue in its interaction with radiation. Various types of phantoms are used to test the performance of medical imaging equipment by mimicking the radiation attenuation and absorption properties of human tissue. Phantoms are also used to measure radiation dosage during therapy, for teaching purposes, to calibrate imaging equipment, and for research purposes. Phantoms are an important element of maintaining high therapeutic and diagnostic quality assurance and control. When applied to image quality control, phantoms are used to measure system resolution, focal spot size, contrast, exposure controls, image artifacts, and the like.

Two classes of phantoms are widely used. One type of phantom uses plastics, gels, water and other chemical mixtures to simulate human tissue and organs. These devices are referred to as "tissue equivalent" phantoms. The other type of phantoms are used to generate test patterns for confirming and evaluating system performance.

Numerous devices for marking, calibrating and aligning images from CAT and MRI systems are known in the art. For example, U.S. Pat. No. 5,299,253 to Wessels describes an alignment system and method to identify a cross-section of an imaged object to facilitate correlation of images. This is especially useful in identifying lesions near organs where a tumor may be obscured by an adjacent organ. U.S. Pat. No. 5,416,816 to Westrup ("Westrup") describes a calibration template for computed radiography. It includes a variety of elements which simulate the X-ray absorption characteristics of various human body portions and organs. The device in Westrup is useful for training radiologists and facilitates standardization of CAT image quality, which is especially useful for remote analysis of transmitted radiographic digital data. This device, however, is of little use in assessing accuracy of table movements which may introduce distortions into the image in a longitudinal direction.

U.S. Pat. No. 3,714,428 of Gasaway discloses a marker for radiology. A radiolucent member having stepped sloping edges with radio-opaque numerals is used to automatically record the height of the visible plane appearing on the film relative to a reference surface. The image of the numeral located closest to the plane is visible on the film while the remaining indicia are obscured.

Most MR imaging centers have some form image quality control that ensures that the acquired images are of sufficient quality for clinical evaluation. Test objects ("phantoms") are often used for this purpose, and a number of investigators have described their application to determinations of the accuracy of volumetric measurements (Tofts et al., *Magn. Reson. Imaging* 1997;15(2):183–92), resolution (Fellner et al. *Magn. Reson. Imaging* 2001 July;19(6):899–904), and relaxation time measurements (Laubach et al., *J. Magn. Reson. Imaging* 1998 8(6):1349–54; Fellner et al., supra; and Kjaer et al., *Acta. Radiol.* 1987 May–June; 28(3): 345–51).

Phantoms have also been used to determine the longitudinal stability (Firbank et al., Br. *J Radiol.* 2000 April; 73(868):376–83) and inter-site stability (Barker et al., *Magn. Reson. Imaging* 1992; 10(4):585–95) of many of these measures.

Phantoms typically have been made of acrylic (Tofts; Firbank; and Fellner, supra), or other non-metallic materials (Tofts, supra; Luft et al., *J. Magn. Reson. Imaging* 1996 July–August; 6(4):700–4; Disler et al., *Invest. Radiol.* 1994 August; 29(8): 739–45; and Laubach et al., *J. Magn. Reson. Imaging* 1998 November–December; 8(6):1349–54), and filled with water (Tofts; and Disler, supra), aqueous solutions of paramagnetic ions (Tofts; Luft; Disler; Laubach; Firbank; Fellner; Kraft et al., *Magn. Reson. Med.* 1987 December; 5(6): 555–62; and Kjaer et al., *Acta Radiol.* 1987 May–June; 28(3):345–51), gels (Lufts; Laubach; Kraft; and Kjaer, supra), vegetable oil (Disler, supra), and other materials that produce an MRI signal.

Such phantoms incorporate a number of shapes and configurations, depending upon their purpose. Among these are cylinders (Tofts; Luft; Disler; and Fellner, supra) cones (Firbank, supra; and Coffey et al., *Med. Phys.* 1989 March–April; 16(2): 273–8), spheres (Disler; and Firbank, supra), and irregular (Lufts; Disler and Lauback, supra) or deformable compartments constructed of, for example rubber (Disler; and Laubach, supra).

Unfortunately, none of the conventional phantoms are well suited for the assessment of quantitative measures of joint cartilage, especially because of they inadequately model cartilage curvature and thinness.

BRIEF SUMMARY OF THE INVENTION

The present invention provides test objects or phantoms that are suited for assessing the quantitative measures of joint cartilage, including cartilage volume, curvature, and thinness. Specifically, the present invention provides phantom that allows for the determination of the longitudinal accuracy and precision of the quantitative measurements of joint cartilage volume and thickness.

In one aspect, the phantoms of the present invention may include an body-within-a-body configuration that produces a three-dimensional, substantially annular space that models important aspects of joint articular cartilage, specifically, its thickness and curvature. Because the phantom has a regular and well-defined shape, it can be precisely described using simple geometric formulae.

In one embodiment, the present invention provides a phantom comprising a housing that has an outside surface and an inside surface. The housing defines a first hollow region therein. A first hollow body is positioned within the hollow region of the housing. The first hollow body comprises an inside surface that defines a second hollow region. A second body having an outside surface is positioned within the second hollow region and is connected to the inside surface of the first hollow body or otherwise positioned within the first body so as to form a space between the outside surface of the second body and the inside surface of the first hollow body. The space is substantially annular and may simulate the shape of joint articular cartilage. Optionally, the phantom may have a stabilizing member that couples the first hollow body and the housing.

By varying the relative size ratio between the first body and second body, the joint cartilage thickness, volume and overall shape may be varied. In such embodiments, the dimension (e.g., radii) of the first body and second body may be manufactured having a defined ratio R. The ratio R is greater than one, and provides the thickness of the simulated cartilage. The value of R is typically between about 1.05 and about 1.2. By having a fixed ratio R along any direction, it is easier to numerically assess the spatial accuracy of the imaging instrument.

Nevertheless, in some embodiments, the ratio between corresponding axes of the first body and second body may be different for at least one of the axes. Moreover, in other embodiments of the present invention, the first body and second body may not be in a defined ratio R.

In some embodiments, the second body may be hollow and may comprise a liquid. Furthermore, the spacing between the first body and the second body may also have a liquid. The liquid within the second body may be the same liquid or a different liquid that fills the space between the first body and second body. The liquids may be air, distilled water, a solution of a contrast enhancing agent, a suspension of a contrast enhancing agent, or the like.

In one specific configuration, the first body comprises a hollow sphere. The hollow sphere is positioned within the hollow region of the housing and has an inside surface that defines a hollow spherical region therein. The second body may be a sphere that is placed inside the first hollow sphere. The second sphere may be anchored at one point to the inside surface of the first hollow sphere. The second sphere has an outside surface that defines a hollow region between the outside surface of the second sphere and the inside surface of the first hollow sphere. A stabilizing member may optionally join the first hollow sphere and the housing. The stabilizing member has a central axis that defines a hollow region therein which communicates with the outside surface of the housing and the hollow region of the first hollow sphere.

As can be appreciated, the present invention need not be practiced with a spherical object. Other relevant shapes may be used instead of spherical bodies. For example, in other configurations, bodies with an elliptical cross-section may be used. Particular utility may derive from the use of shapes with elliptical cross section on planes that contain a semi-major axis. For example, the elliptical body can have an elliptical cross-section in planes that contain all three axes of the body. Additionally, the elliptical body can have an elliptical cross-section along a plane that contains one axis and a circular cross-section in a plane that contains another orthogonal axis.

The elliptical bodies may comprise two equal orthogonal radii and a third orthogonal radius of different dimension, or three orthogonal radii of different dimension. The dimensions of the hollow elliptical bodies may be scaled by the factor R. As can be appreciated, R may be the same along each axis of the elliptical body or it may vary for each axis.

Other aspects, objects and advantages of the invention will be apparent from the detailed description that follows.

DETAILED DESCRIPTION OF THE INVENTION

Figure 1:
FIG. 1 shows magnetic resonance images of a human knee: a), b), and c) are axial, sagittal, and coronal, respectively, that show the overall anatomy, with femur (F), patella (P), tibia (T), and articular cartilage (arrows) indicated. Panel d) is one sagittal slice from a set of 3-D gradient-recalled-echo images in which the high signal due to fat has been selectively attenuated ("fat saturation") so that bone marrow is relatively hypointense and articular cartilage is hyperintense (cf. a)-c))

Magnetic Resonance Imaging (MRI) has been used for some time to assess the status of joints, particularly the knee, in a variety of clinical circumstances, including osteoarthritis (Stoller D W in "Clinical Magnetic Resonance Imaging", Edelman RR, Heslink J R, Slatkin M B, eds, W. B.Saunders Co., Philadephia, $2^{nd}$ edn, 1996, Chap. 61 "Knee", pp. 1954–2003). MRI of the knee provides excellent visualization of all aspects of the knee joint, including cartilage, synovium and subchondral bone (FIG. 1). This visualization capability combined with the three dimensional tomographic nature of MRI makes it a favorable technology for use in the evaluation of osteoarthritis.

In particular, cartilage volume and cartilage measurements made from MR images acquired over time may provide a quantitative measure to assess disease status and response to therapy in this slowly progressing degenerative disease. An understanding of the precision of these measures is necessary to be able to design studies involving the longitudinal assessment of degenerative change in the knee in clinical trials (Peterfy C G, Semin. Musculoskelet. Radiol. 2001 December; 5(4):365–78).

The present invention provides a test object ("phantom") useful for determining the dimensional (volume) accuracy and precision of the quantitative measurements of joint cartilage volume and thickness. The phantoms of the present invention include a first hollow body that receives a second body. The second body is disposed in an offset position within the first body so as to produce a three-dimensional space that models aspects of joint articular cartilage, specifically, its thickness and curvature. Because the phantom has a regular and well-defined shape, it can be precisely described using simple geometric formulae.

The phantoms of the present invention may include a housing that has an outside surface, an inside surface and a central axis defining a hollow region therein. In preferred embodiments, at least one surface of the housing will be flat so as to facilitate positioning of a definable axis with the imaging planes of the imaging system. The hollow region of the housing may receive the first hollow body, such as a hollow sphere or elliptical body. The first hollow body defines an inside surface that defines a hollow space. The second body, such as a sphere or ellipse, is located within the hollow space of the first hollow body. The diameter or outside perimeter of the second body is smaller than that of the first hollow body. The second body defines an outer surface and may be anchored at a point within the inside surface of the first hollow body, so that the first body and second body are asymmetrically offset from each other. Consequently, the outer surface of the second body and the inner surface of the first hollow body define a hollow region between the outer surface of the second body and the inner surface of the first body that mimics the shape of joint articular cartilage.

In one exemplary embodiment, the phantom comprises sphere-within-a-sphere configuration. In other embodiments, the phantom comprises an elliptical body-within an-elliptical body configuration. It should be appreciated however, that while the spheres and ellipses better approximate the knee anatomy, the present invention is not limited to sphere's and elliptical bodies. The phantoms of the present invention may comprise a variety of other symmetrical or asymmetrical bodies disposed within each other.

The first body is hollow and the second body may be hollow or solid. When the second body is hollow, it may be filled with air or it may contain a liquid, a gel (e.g., agarose, gelatin, agar, polyvinyl alcohol, silicone, polyacrylamide), a solution, a suspension, or other conventional signal bearing material. The gel or liquid may include a dissolved or suspended contrast agent. The liquid is preferably a member selected from water (e.g., distilled water), a solution of a contrast enhancing agent, a suspension of a contrast enhancing agent and combinations thereof. As can be appreciated, after the second body is positioned within the first body, the hollow space within the first body may thereafter be filled with a liquid or solid material.

The first hollow body may be fixedly attached to the housing. Typically the first body is attached to the housing with a stabilizing member that runs from the housing to the outside surface of the first hollow body. In one configuration, the stabilizing member is a hollow tube that creates a fluid conduit between the outside surface of the housing and the inside surface of the first hollow body. The arrangement of the hollow tube in relation to the other components of the phantom allows for adding a liquid to or removing a liquid from the first hollow body of the phantom. One of skill will appreciate that multiple solid or hollow tubes in any configuration can be utilized as support members for the hollow body. As such, in embodiments in which the second body is hollow, if desired, a second hollow tube may optionally be used to create a fluid conduit between the outside surface of the housing and a hollow region of the second body.

When the phantom of the invention includes a contrast enhancing agent, it is well within the abilities of one of skill to select an appropriate contrast agent and an appropriate concentration of the contrast agent for a given application. Exemplary phantoms of the invention may include one or more contrast enhancing agents selected from an X-ray contrast agent, a CAT contrast agent, an ultrasound contrast agent and a magnetic resonance imaging (MRI) contrast agent. Moreover, a phantom of the invention may include more than one type of contrast agent for the same or different imaging modalities.

Contrast agents are useful adjuncts in radiological imaging, making it possible to determine the location, size and conformation of organs or other structures of the body in the context of their surrounding tissues. Exemplary X-ray contrast agents include insoluble inorganic barium salts, which enhance X-ray attenuation in the body zones into which they distribute. Other X-ray contrast agents include soluble iodine containing compounds such as those marketed by Nycomed Imaging A.S. under the trade names Omnipaque® and Amipaque®. Much recent work on X-ray contrast agents has concentrated on aminopolycarboxylic acid (APCA) chelates of heavy metal ions.

MRI contrast agents are typically based on paramagnetic metal chelates or ferri- or ferro-magnetic particles. Chelates with high thermodynamic and kinetic stabilities are preferred since their ability to remain stable in vivo offers a distinct benefit to MR imaging and to the constructs of the present invention. Exemplary chelating agents include 1,4,7,10-tetraazacyclododecane-N,N',N'',N'''-tetraacetic acid (DOTA). Further examples are 1,4,7,10-tetraazacyclododecane-N,N',N''-triacetic acid (DO3A), diethylene-triamine-pentaacetic acid (DTPA) and various analogs and derivatives of both ligands.

Chelated or unchelated paramagnetic metal ions are of use in the phantoms of the present invention. Paramagnetic metals of a wide range are suitable for complexation with these ligands. Suitable metals are those having atomic numbers of 22–29 (inclusive), 42, 44 and 58–70 (inclusive), and have oxidations states of 2 or 3. Those having atomic numbers of 22–29 (inclusive) and 58–70 (inclusive) are preferred, and those having atomic numbers of 24–29 (inclusive) and 64–68 (inclusive) are more preferred. Examples of such metals are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Manganese (II), iron (III) and gadolinium (III) are particularly preferred, with gadolinium (III) the most preferred.

Wherein the phantom is designed for use in conjunction with MR imaging, the contrast enhancing agent may be a chelate of a paramagnetic lanthanide ion, which is preferably water soluble. The solution of chelate in the phantom generally has a concentration of from about 0.025M to about 2.5M.

When the phantom is designed for us in conjunction with nuclear imaging, the contrast enhancing agent may be a short-lived radioactive agent, such as Tc-99m or Th-201, or a positron emitter such as F-18, or a sealed solution with a longer-lived agent such as Cd-109 (a radioactive surrogate for Tc-99 m), Ge-68 (a long-lived positron emitter), and the like. For ultrasound, the phantom may contain a high-viscosity liquid with a suspension of micro-particles, where the size and concentration of the particles establish an image contrast.

As can be appreciated, for any of the above embodiments the hollow first body and the second body may contain the same material or different materials, depending on the desired attenuation, absorption, or emission properties.

The phantoms of the invention may be configured to model various regions and tissues within a mammalian joint. In a preferred example, the phantom is configured to model articular cartilage of a mammalian joint, preferably a knee joint.

The phantom can be utilized to model any property of a constituent or array of constituents of the mammalian joint. For example, properties of articular cartilage that are modeled using a phantom of the invention include the thickness of the cartilage, the curvature of the cartilage and a combination thereof.

The phantom is intended to be imaged at regular intervals over the entire time period (e.g., months to years) that a given patient or group of patients is to be studied. The images and measurements derived from the phantom are used to check the accuracy and dimensional precision of corresponding images and measurements derived from patients and correct them as necessary. Accurate measurements of known precision are important in tracking small changes in disease state and response to therapy.

The phantoms of the present invention may be used in conjunction with an array of diagnostic and treatment modalities, including CT, MRI, ultrasound, x-ray and nuclear medicine. In each of the various modalities, the phantoms of the present invention may be used to test system performance, evaluate the repeatability of results obtained during the procedure, and compensate for any "drift" or change in the parameters of the procedure. Changes in procedure parameters arise from a variety of sources including, but not limited to, environmental sensitivity of the device, component drift, change in operating parameters, change to the hardware and the software introduced during service and/or upgrade procedures by the manufacturer, etc.

The phantoms of the invention may also be of use in image quality control to, for example, compensate for noise, assess spatial resolution, sensitivity, slice thickness, focal zone, system sensitivity, gray scale, dynamic range, penetration, dead zone, dose, etc.

When the phantoms of the invention are used in conjunction with a nuclear medicine procedure, the phantom is useful to assess the performance of gamma cameras (single photon emission computed tomography and positron emission tomography) for field uniformity, volume sensitivity, spatial resolution, lesion detectability, etc.

The phantoms of the invention are useful for quality control, calibration and testing of radiographic, fluoroscopic, tomographic and angiographic equipment. The phantom is used to evaluate the system for contrast, resolution, image quality, image, intensifier performance, and exposure.

The phantom of the invention can also be used in conjunction with radiotherapy. The phantom may be utilized to measure radiation dose, dose distributions, and other treatment parameters.

FIGS. 2A to 4 illustrate one exemplary phantom 10 of the present invention. The phantom 10 includes a housing 12 that comprises an inner surface 11 and an outer surface 13. Inner surface 11 defines a hollow region 15 that has a central axis 14. In one configuration, housing 12 comprises an acrylic cylindrical body and the central axis 14 runs longitudinally through the cylindrical body.

The housing material should be compatible with the imaging modality in use. For example, the housing material typically does not unduly absorb x-rays when used in nuclear imaging or x-ray CT, and it should not introduce magnetic field distortions or RF shielding when used in MRI. Thuse, desirable characteristics f or a general use phantom are non-conductivity (which generally rules out carbon fibers, fiberglass, and glasses) and a low atomic number and density, coupled with suitable strengths. Thus, some useful materials are acrylics, LUCITE®, LEXAN®, some PVCS, and the like. Such materials are well known to those of ordinary skill in the art.

Figure 2A:
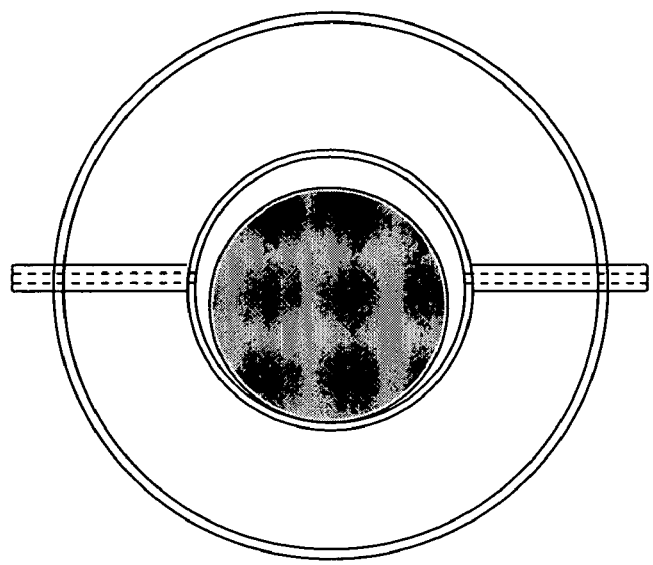
FIG. 2A is an end view of one embodiment of a phantom of the present invention.
Figure 2B:
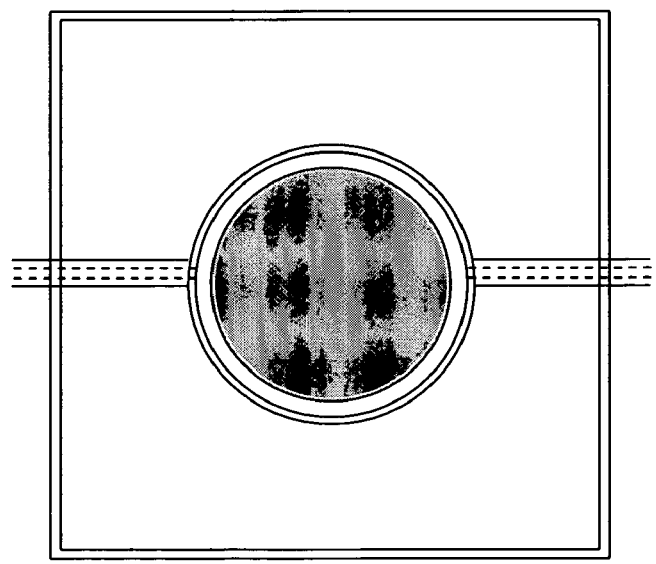
FIG. 2B is a top view of the phantom of FIG. 2A.

A first hollow body 16 is fixedly positioned inside a hollow region 15 of cylindrical housing 12. First hollow body 16 comprises an inner surface 17 and an outer surface 18. The inner surface 17 defines a hollow region 19 within the first hollow body 16. As shown in FIGS. 2A and 2B, the first hollow body 16 is typically positioned centered about the central axis 14 within the hollow region 15 of housing 12.

Typically, first hollow body 16 is held in place within the housing 12 by means of one or more support members 20. Optionally, support member 20 may be hollow so as to provide a fluid conduit from the exterior of the housing 12 to a hollow region 19 of the first hollow body 16 so as to allow a material (such as a contrast agent) to be deposited and removed from first hollow body 16. As can be appreciated, the present invention is not limited to the use of support members 20, and other support members maybe used.

A solid or hollow second body 22 may be positioned within the hollow region 19 of the first hollow body 16. The dimensions of second body 22 will be smaller than the dimensions of the first hollow body 16. The size ratio R between the first body 16 and the second body 22 (e.g., the inner radius of the inner surface 17 of the first hollow body 16 to the outer radius of an outer surface 24 of the second hollow body 22) is greater than one to one, and is preferably between about 1.05 and about 1.2.

A portion 28 of the outside surface 24 of second hollow body 22 may be anchored to a point on the inner surface 17 of the first hollow body 16 or the second body 22 may otherwise be positioned within hollow region 19 so as to position the second body 22 offset from the first hollow body and offset from the central axis 14 of housing 12. Such a positioning creates a non-symmetrical space 26 between the inner surface 17 of the first hollow body 16 and the outside surface 24 of the second body 22. As noted above, Applicants have found that the offset positioning between the first body 16 and second body 22 creates the non-symmetrical space 26 that closely mimics the joint articular cartilage of the knee.

The space 26 corresponds to the cartilage of the knee joint. The thickness and curvature of the cartilage may be modified by changing the relative shapes of the first and second bodies 16, 22 and the relative sizes of the first and second bodies 16, 22. For example, if it is desired to have a thinner cartilage, the first body and second body may have a size ratio R that is close to one to one. If however, it is desired to portray a thicker cartilage, the size ratio R may be between about 1.05 and about 1.2. As can be appreciated, any size ratio R above 1.0 may be used with the phantoms of the present invention.

The volume of space 26 (e.g. cartilage) may easily be calculated by subtracting the volume of the second body 22 from the volume of the hollow region 19 defined by the inner surface 17 of the first body. During imaging, the known volume of the space 26 may be compared to the volume calculated by the imaging software to determine the accuracy of the software's calculation.

While FIGS. 2A to 4 show the first body 16 and second body 22 as spheres, it should be appreciated that the phantoms 10 of the present invention are not limited to spheres. For example, as shown in FIGS. 5A and 5B, the first body 16 and second body 22 may comprise elliptical bodies. The elliptical body 16, 22 has well defined dimensions defined generally by its three orthogonal radii. The elliptical bodies used in the phantoms of the present invention may have two orthogonal radii of equal dimension and a third orthogonal radius of a different dimension, or the phantoms may have three orthogonal radii that all have different dimensions. The first and second elliptical bodies 16, 22 will typically (but not necessarily) have similar size ratios R as the spherical first body 16 and spherical second body 22.

The elliptical first hollow body 16 and elliptical second body 22 may provide additional benefits that aren't provided by the spherical bodies. For example, when used to test spatial resolution in a tomographic device, it is often the case that the resolution of the tomographic device is different along different orthogonal directions. For instance, in CT scanners it is often the case that the spatial resolution along the slice direction is poorer than in plane. In MRI, all three directions may have different spatial resolution, depending on the clinical problem. Having different spatial resolution can result in asymmetrical conditions. By scaling the dimensions and configuration of the test phantom 10 to the spatial resolution of the tomographic device, the sampling becomes more uniform along all three axes. For example, if the slice thickness of the tomographic device is 5× in the in-plane resolution, then the phantom may be manufactured to have a 5× radius along a longitudinal axis of the tomographic device. Thus, the resolving power of the tomographic device will be substantially the same for an appropriately matched phantom. In some circumstances, this permits an unbiased evaluation of the performance of the tomographic device.

For example, one of the quantities that is used to define a tomographic device is the crosstalk between adjacent pixels, e.g., the amount of signal in one pixel that sheds onto its neighbor pixels. The crosstalk is observed as, for instance, a graying of what should be a dark pixel. By providing the same sampling along the three axes of the tomographic device means that the same amount of signal spill-over represent the same amount of crosstalk.

Further details of the configuration of an exemplary phantom of the invention are provided in the examples set forth hereinbelow. The following examples are offered to illustrate a selected embodiment of the invention, not to limit the scope of the invention.

EXAMPLE 1

Figure 3:
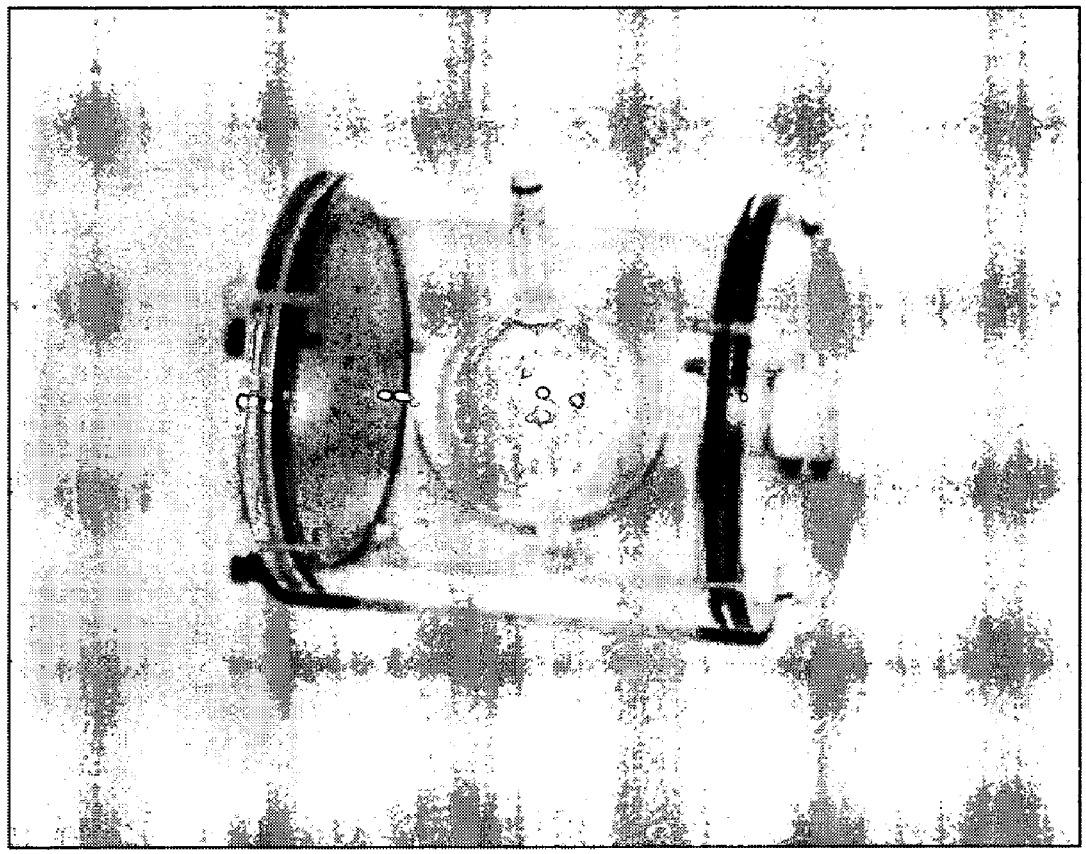
FIG. 3 is an elevational photograph of one exemplary phantom of the present invention.

The phantom is constructed of acrylic. The phantom shown in FIGS. 2A and 2B comprise a 4 inch diameter by 4 inch long (101.6 mm×101.6 mm) cylinder housing 12 containing a hollow 2.25 inch (57.2 mm) inner diameter sphere 16 that is fixedly held in place within the cylinder housing 12 by two hollow rods 20 that communicate with the space inside the sphere 16. Attached to the inner surface 17 of the sphere 16 is a 2 inch (50.8 mm) diameter solid sphere 22. The dimension tolerance was 0.005 in. (0.1 mm). FIG. 3 is a photograph of the completed phantom 10. The hollow rods 20 that support the outer, hollow sphere 16 within the cylindrical housing 12 were used to completely fill the space 26 between the solid inner sphere 22 and the hollow outer sphere 16 with a liquid, such as distilled water. The weight of the water required divided by its density (0.998 at 22° C.; Handbook of Chemistry and Physics, CRC Press, Boca Raton, Fla.) gave its volume. For imaging, the water was replaced with 0.25 mM Gd-DTPA solution (Magnevist, Berlex Laboratories, Wayne, N.J.), and the body of the phantom was filled with distilled water.

Imaging was done using a 1.5 Tesla GE Signa LX system (GE Medical Systems, Milwaukee, Wis.) and an extremity coil (Medical Advances, Inc., Milwaukee, Wis.). The accuracy and precision of MRI spatial measurements are fundamentally determined by the magnetic field gradients that are used to encode the information in the image. The particular imager that was used in the method presented herein was serviced monthly by a GE Field Engineer who adjusted the gradients to within 0.5 mm in 100 mm, or 0.5%. The observed 1-pixel (0.5 mm) precision of in-plane measurements of the phantom agreed with this value. Likewise, the calculated slice thickness (2.00±0.09 mm) equaled the nominal slice thickness (2 mm).

A 3D-SPGR sequence (TR/TE/Flip 58 ms/6 ms/40°; 12 cm×12 cm FOV; 60 contiguous 2 mm slices; 256×192; 1 NEX) was used to obtain a set of images depicting the entire phantom in three dimensions.

The image data were transferred to a Sun workstation (Sun Microsystems, Palo Alto, Calif.) for display and analysis using MRVision software (MRVIsion, Inc., Wakefield, Mass.). To determine the volume of the substantially annular space 26 in the spherical phantom 10, ROI's in each slice of the 3D data set were manually segmented using a seed-growing algorithm, and the resulting area was multiplied by the slice thickness to yield the volume. This segmentation was repeated four times, and coefficients of variation (CV=mean/standard deviation) were calculated for the total volume, and for each slice.

Figure 4A:
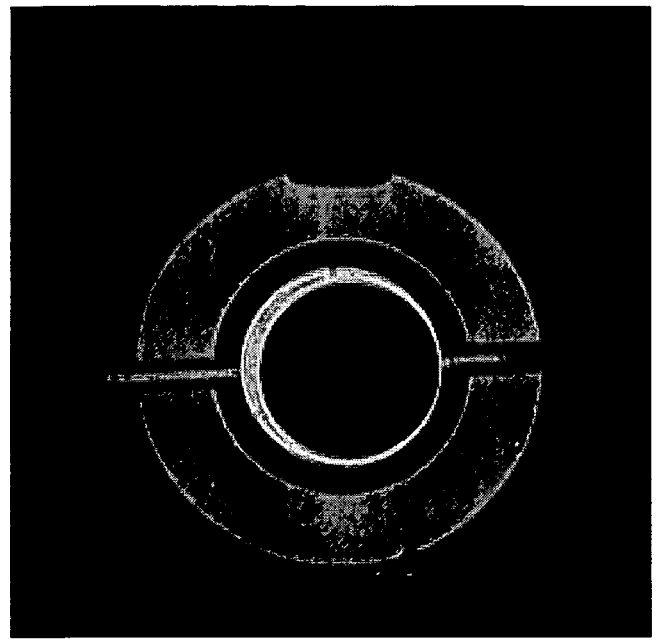
FIG. 4A shows an end view MR image of an exemplary phantom of the present invention.
Figure 4B:
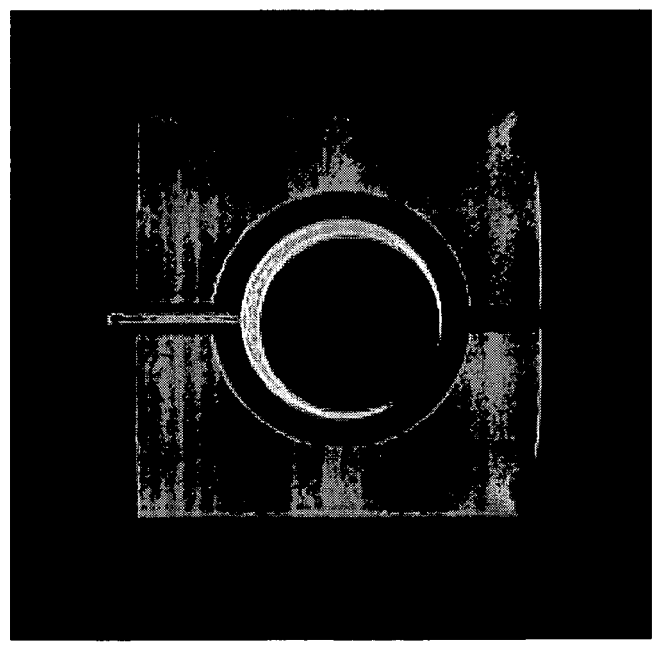
FIG. 4B is a top view of an MR image of an exemplary phantom of the present invention.
Figure 5A:
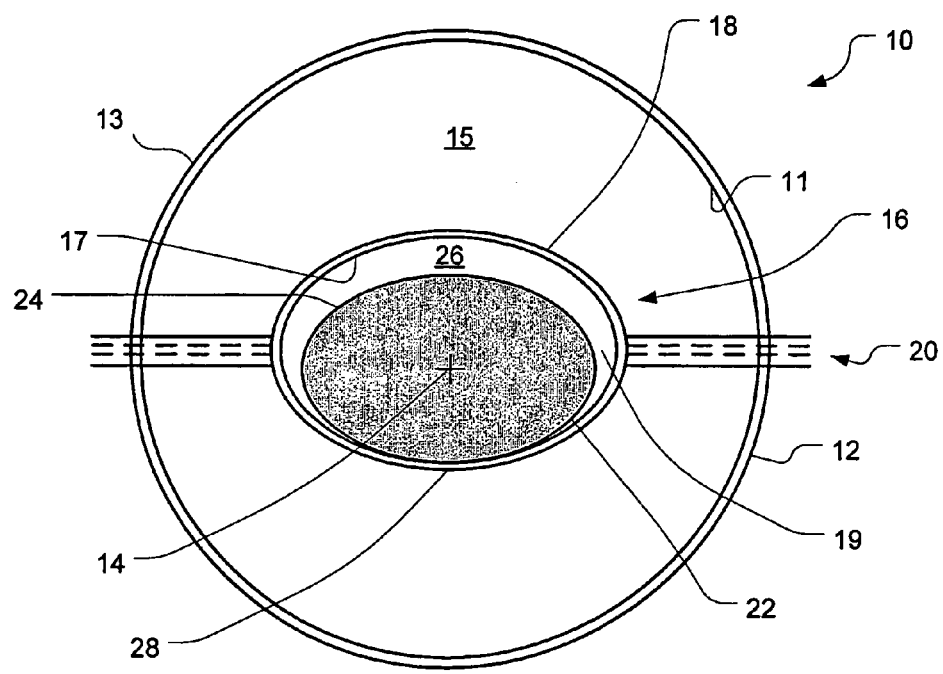
FIG. 5A is an end view of another embodiment of a phantom that is encompassed by the present invention.
Figure 5B:
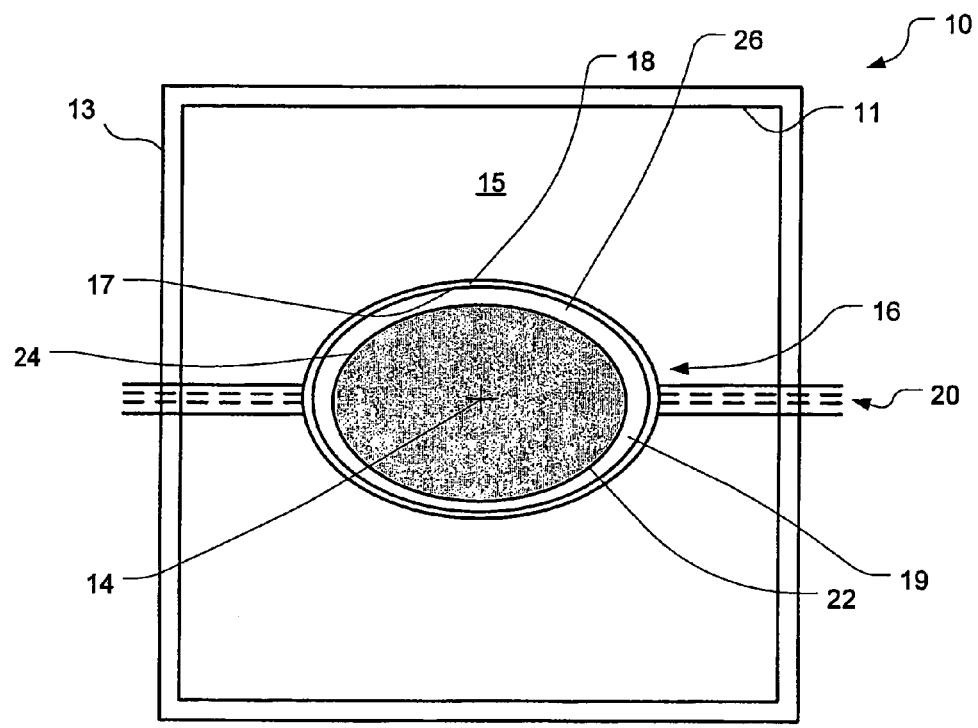
FIG. 5B is a top view of the phantom of FIG. 5A.

Cross-sectional MR images of the phantom are shown in FIGS. 4A and 4B. The water-filled space 26 between the two spheres 16, 22 appears as a high intensity crescent in those slices that pass through their point of contact, and an annulus or circle in other slices. The volume of this space 22 determined from its contained mass of water was 30.1 $cm^3$±0.2 $cm^3$. Four replicate measurements of a single MRI data set gave values of 31.0, 29.7, 28.9, and 29.4 $cm^3$. The mean (sd) MRI volume was 29.8 $cm^3$ (0.9 $cm^3$), or 98.8% (3.0%) of the actual volume. The CV of the total volume was 3.03%. The slice root-mean-square CV was 9.35%.

In-plane linear measurements were accurate to one pixel, or 0.5 mm.

EXAMPLE 2

Partial volume averaging is another source of error, especially when measuring a curved object using rectilinear voxels. However, the partial volume error can be calculated for the phantoms of the present invention, since its size and shape are precisely known. If one assumes ideal voxels of 0.5 mm×0.5 mm×2 mm and ideal segmentation, the total voxel volume of a sphere of radius 24 mm is 99.98% of the true volume. In such calculations, all voxels whose centers lie within the sphere are counted as sphere. All voxels whose centers lie outside of the sphere are not counted, although they may contain part of the sphere. This corresponds to a segmentation threshold of about 50%.

The measured volume of the partially annular space 26 (the model "cartilage") in the spherical phantom was 98.8% ±3.0% of the true value. This total error (1.2%) is greater than the estimated partial volume error (0.02%) and comparable to the cumulative error in the gradients (3×0.5%=1.5%). These results can be used to calculate a correction factor (in this case, 1.02) and estimate a precision for in vivo measurements done at approximately the same time.

It is understood that the examples and embodiments described herein are for illustrative purposes only and that various modifications or changes in light thereof will be suggested to persons skilled in the art and are to be included within the spirit and purview of this application and scope of the appended claims. For example, in other embodiments, it may be possible to have the first body 16 and second body 22 be different shapes all together. For example, in one embodiment, the first body may be an ellipse and the second body may be a sphere. Numerous different combinations are possible, and such combinations are considered to be part of the present invention. All publications, patents, and patent applications cited herein are hereby incorporated by reference in their entirety for all purposes.

What is claimed is:

1. A phantom comprising:
    a housing comprising an outside surface, an inside surface, said housing defining a first hollow region therein;

a first hollow body positioned within said hollow region of said housing, said first hollow body comprising an inside surface that defines a second hollow region;

a second body comprising an outside surface, said second body being positioned within the second hollow region and connected to said inside surface of said first hollow body, wherein the positioning of said second body relative to the first hollow body forms a spacing between said outside surface of said second body and said inside surface of said first hollow body; and a stabilizing member coupling said first hollow body and said housing.

2. The phantom according to claim 1, wherein said stabilizing member comprises a central axis defining a hollow region therein that provides a fluid path from outside of the housing to said first hollow region of said first hollow body.

3. The phantom according to claim 1, wherein said second body is hollow.

4. The phantom according to claim 3, wherein said second body comprises a liquid.

5. The phantom according to claim 4, wherein said second hollow body and said first hollow body each contain a different liquid.

6. The phantom according to claim 4, wherein said liquid comprises distilled water, a solution of a contrast enhancing agent, or a suspension of a contrast enhancing agent.

7. The phantom according to claim 6, wherein said contrast enhancing agent is a member selected from an X-ray contrast agent, an x-ray CT contrast agent, an ultrasound contrast agent, a magnetic resonance imaging contrast agent, and a radionuclide solution.

8. The phantom according to claim 7, wherein said contrast enhancing agent is a chelate of a paramagnetic lanthanide ion.

9. The phantom according to claim 8, wherein said chelate of a paramagnetic lanthanide ion is present in a concentration of from about 0.025M to about 2.5M.

10. The phantom according to claim 1, wherein said second body is solid.

11. The phantom according to claim 1, wherein the first body and second body comprise a first spherical body and a second spherical body, respectively.

12. The phantom according to claim 11, wherein the first spherical body and second spherical body each define a radius, wherein the radii have a ratio of R that is between about 1.05 and about 1.2.

13. The phantom according to claim 1, wherein the first body and second body comprise a first elliptical body and a second elliptical body, respectively.

14. The phantom according to claim 13, wherein the first elliptical body and second elliptical body define three orthogonal radii, wherein each of the corresponding sets of radii of the first and second elliptical body are provided in a substantially equal ratio R.

15. The phantom according to claim 13, wherein the first elliptical body and second elliptical body define three orthogonal radii, wherein at least two of the corresponding sets of radii of the first and second elliptical body are provided in different ratios.

16. The phantom according to claim 13, wherein the first elliptical body and second elliptical body each define three orthogonal radii, wherein the radii are provided in a direct proportion to a spatial resolution along a corresponding axis of a target tomographic imaging device.

17. The phantom according to claim 13, wherein the first and second elliptical bodies each comprise three orthogonal radii, wherein the orthogonal radii comprise two orthogonal radii of equal dimension and a third orthogonal radii of a different dimension.

18. The phantom according to claim 13, wherein the first and second elliptical bodies each comprise three orthogonal radii, wherein at least one of the first and second elliptical body comprises orthogonal radii that are all different dimensions.

19. The phantom according to claim 18, wherein the radii of the first elliptical body and the corresponding radii of the second elliptical body are in a ratio R that is between about 1.05 and about 1.2.

20. The phantom according to claim 1, wherein the housing comprises a central axis, wherein the first hollow body is symmetrically positioned about the central axis and the second body is not symmetrically positioned about the central axis.

21. The phantom according to claim 1, wherein the housing comprises a cylinder.

22. The phantom according to claim 1, configured to model articular cartilage of a mammalian joint.

23. The phantom according to claim 22, wherein said joint is a human knee joint.

24. The phantom according to claim 22, wherein a member selected from thickness of said cartilage, curvature of said cartilage and a combination thereof is modeled.

25. An asymmetrical phantom comprising:

a housing comprising an outside surface, an inside surface, said inside surface of the housing defining a first hollow region therein;

a first hollow elliptical body fixedly positioned within said hollow region of said housing, said first hollow elliptical body comprising an inside surface that defines a second hollow region; and a second elliptical body comprising an outside surface, said second elliptical body being positioned within the second hollow region and connected to said inside surface of said first hollow elliptical body, wherein the positioning of said second body elliptical body relative to the first hollow elliptical body forms a spacing between said outside surface of said second elliptical body and said inside surface of said first hollow elliptical body.

26. The phantom according to claim 25, wherein said second elliptical body is hollow.

27. The phantom according to claim 26, wherein the first hollow elliptical body and the second hollow elliptical body each comprise a liquid.

28. The phantom according to claim 27, wherein the liquid in the first hollow elliptical body is a different from the liquid in the second hollow elliptical body.

29. The phantom according to claim 27, wherein the first and second elliptical bodies each comprise three orthogonal radii, wherein the orthogonal radii comprise two orthogonal radii of equal dimension and a third orthogonal radii of a different dimension.

30. The phantom according to claim 27, wherein the first and second elliptical bodies each comprise three orthogonal radii, wherein the orthogonal radii all comprise different dimensions.

31. The phantom according to claim 25, wherein said first hollow elliptical body is fixedly positioned within said hollow region of said housing with a stabilizing member, wherein said stabilizing member comprises a first rod and a second rod, wherein the first rod comprises a hollow region therein that provides a fluid path from outside of the housing to said first hollow region of said first hollow body, and the second rod comprises a hollow region therein that provides a fluid path from outside of the housing to a hollow region of the second hollow elliptical body.

32. The phantom according to claim 25, wherein the first elliptical body and second elliptical body define three orthogonal radii, wherein each of the corresponding sets of radii of the first and second elliptical body are provided in a substantially equal ratio R.

33. The phantom according to claim 25, wherein the first elliptical body and second elliptical body define three orthogonal radii, wherein at least two of the corresponding sets of radii of the first and second elliptical body are provided in different ratios from the third set of radii.

34. The phantom according to claim 25 wherein the first elliptical body and second elliptical body each define three orthogonal radii, wherein the radii are provided in a direct proportion to a spatial resolution along a corresponding axis of a target tomographic imaging device.

* * * * *